United States Patent [19]

Rajaiah et al.

[11] Patent Number: 5,543,443
[45] Date of Patent: Aug. 6, 1996

[54] DENTURE STABILIZING COMPOSITIONS

[75] Inventors: Jayanth Rajaiah, Loveland, Ohio; Abel Saud, Milford, Conn.; Bruce J. MacKay, Cincinnati, Ohio; Dennis R. Grubbs, Atizapan, Mexico

[73] Assignee: The Procter & Gamble Company, Cincinnati, Ohio

[21] Appl. No.: 904,782

[22] Filed: Aug. 3, 1992

Related U.S. Application Data

[63] Continuation-in-part of Ser. No. 825,885, Jan. 27, 1992, abandoned.

[51] Int. Cl.⁶ .......................... A61K 6/093; C08L 33/00; C08L 83/00
[52] U.S. Cl. .................. 523/120; 523/116; 523/118; 524/28; 524/31; 524/45; 524/55; 524/261; 524/267; 524/377; 524/522; 524/557; 525/100; 525/101; 525/102; 525/207; 525/328.9; 525/366; 525/477; 525/478; 525/479; 525/474; 526/279; 528/15; 528/26; 528/31; 528/32; 528/33; 528/374; 522/148
[58] Field of Search ................... 524/45, 55, 377, 524/261, 267; 523/120, 116, 118, 120; 525/100, 101, 102, 474, 207, 328.9, 366, 477, 478, 479; 522/148

[56] References Cited

U.S. PATENT DOCUMENTS

| | | | |
|---|---|---|---|
| 3,889,385 | 6/1975 | Dougherty | 32/12 |
| 4,082,693 | 4/1928 | Kessler et al. | 528/374 |
| 4,284,539 | 8/1981 | Homan et al. | 528/15 |
| 4,373,036 | 2/1983 | Chang et al. | 523/120 |
| 4,529,748 | 7/1985 | Wienecke | 523/120 |
| 4,657,959 | 4/1987 | Bryan et al. | 524/266 |
| 4,831,070 | 5/1989 | McInally et al. | 524/267 |
| 4,965,295 | 10/1990 | Schwabe et al. | 523/120 |
| 4,970,245 | 11/1990 | Futami et al. | 523/109 |
| 4,980,391 | 12/1990 | Kumar et al. | 524/45 |
| 5,037,638 | 8/1991 | Hamer et al. | 424/52 |
| 5,037,924 | 8/1991 | Tazi et al. | 526/272 |
| 5,073,604 | 12/1991 | Holeva et al. | 525/327.8 |
| 5,075,107 | 12/1991 | Katakura et al. | 523/120 |
| 5,086,148 | 2/1992 | Jochum et al. | 525/478 |
| 5,093,387 | 3/1992 | Schobel et al. | 523/120 |
| 5,308,887 | 5/1994 | Ko et al. | 522/148 |

FOREIGN PATENT DOCUMENTS

| | | | |
|---|---|---|---|
| 0398745 | 11/1990 | European Pat. Off. | C08L 83/07 |
| 60-132551 | 7/1985 | Japan | A61C 13/16 |
| 3-168143 | 7/1991 | Japan | A61C 13/23 |
| 4-29906 | 1/1992 | Japan | |
| 4-149110 | 5/1992 | Japan | |
| 4-149108 | 5/1992 | Japan | |
| 427705 | 2/1975 | U.S.S.R. | A61C 9/00 |
| 2272905 | 6/1994 | United Kingdom | 523/118 |

*Primary Examiner*—Paul R. Michl
*Assistant Examiner*—Olga Asinovsky
*Attorney, Agent, or Firm*—Mary Catherine Poland; Douglas C. Mohl; Jacobus C. Rasser

[57] ABSTRACT

Disclosed are denture adhesive compositions possessing improved aesthetics and comprising a component which provides for easy removal of the adhesive from the denture and a hydrophilic powder.

16 Claims, No Drawings

DENTURE STABILIZING COMPOSITIONS

This is a continuation-in-part application of application Ser. No. 825,885, filed Jan. 27, 1992 now abandoned.

TECHNICAL FIELD

This invention relates to improvements in adhesives, in particular, improved denture adhesives.

BACKGROUND OF THE INVENTION

Ordinary removable dentures, dental plates, and the like, comprise teeth mounted in a suitable plate or base. Dentures function as a substitute for missing teeth and serve as a replacement for all or a portion of the teeth ordinarily found in the oral cavity. Although dentures generally are skillfully prepared, often they do not fit perfectly. Moreover, no matter how satisfactory at first, after a period of time the fit of the denture becomes loose and imperfect due to natural shrinkage and changes in the gums, mucous tissues, and the like. Loose and imperfectly fitted dentures usually are corrected and stabilized by the use of a denture adhesive. Denture adhesives are used to fill the interstices between the dentures and the gums or tissues. Prior to placement of the denture in the oral cavity, a denture adhesive is applied to the denture-plate surface which, for a perfect fit, should uniformly contact the gums and mucous tissues. The denture adhesive is formulated not only for its adherent properties, but also to provide a cushion or gasket between the denture and the gums or tissues, thereby positioning the denture securely in the oral cavity.

Requirements and characteristics for a satisfactory denture adhesive composition are many and are dictated by numerous factors. Desirably, one daily application of such a composition should function as an effective means for insulating, cushioning, and securely positioning the denture. The composition should retain its characteristics and properties in the typical powder and cream forms during storage under various climatic conditions taste; optionally provide antiseptic and germicidal properties for preventing or inhibiting the growth of organisms ordinarily found in the mouth; and function as an agent for prevention of putrefaction or malodorous decomposition of foods or secretions lodging beneath or adjacent to the denture. The adhesive material must be capable of imbibing water and saliva and swelling, so as to essentially fill the interstices between the denture and the gum or mucous tissues. The adhesive should not attack or damage the denture, as by causing a crazing of the denture-plate material. Additionally, the adhesive should be stable to bacteria, molds and enzyme systems found in the oral cavity, and have a pH that is nonirritating to the oral mucosa, generally 5–8.5, preferably a pH around 7.0. The mechanical strength of the adhesive mass, be it gel or colloid, formed by imbibition of water should be great enough to securely maintain the position of the denture under normal use, and not so great as to make denture removal difficult when desired, or as to damage or injure the gums, tissues or denture upon removal.

There has been a considerable effort made over many years to develop improved denture adhesives. Both synthetic and natural polymers and gums have been used singly, in combination, and in combination with various additives.

European Patent 64,672 to Dhabhar and Schmidt, published Nov. 17, 1982, relates to a hydrophilic denture adhesive containing an adhesive polymeric fraction comprising CMC and poly(ethylene oxide) in a hydrophilic vehicle.

European Patent Application 140,486 to A. J. Desmaris, filed Jul. 31, 1984 relates to denture adhesive compositions containing a hydrophobically modified water-soluble polymer, alone or admixed with an alkali metal salt of CMC. Hydrophobically modified hydroxyalkyl celluloses and copolymers of ethylene oxide and long chain epoxyalkanes are preferred for use in the compositions.

U.S. Pat. No. 4,280,936 to Dhabhar, Heyd and Schmidt (issued Jul. 28, 1981), relates to improved denture adhesives containing a specified ratio of CMC and poly(ethyleneoxide) in a mineral oil base.

U.S. Pat. No. 4,474,902 to Dhabhar and Schmidt (issued Oct. 2, 1984), relates to improved denture adhesives containing karaya gum in a hydrophilic vehicle. See also U.S. Pat. No. 4,514,528 (issued Apr. 30, 1985) specified ratio of CMC and poly(ethyleneoxide) in a mineral oil base.

U.S. Pat. No. 4,474,902 to Dhabhar and Schmidt (issued Oct. 2, 1984), relates to improved denture adhesives containing karaya gum in a hydrophilic vehicle. See also U.S. Pat. No. 4,514,528 (issued Apr. 30, 1985) and U.S. Pat. No. 4,518,721 (issued May 21, 1985) to these same inventors, relating, respectively, to improved denture adhesives containing adhesive polymeric fractions consisting of admixtures of partial salts of lower alkylvinyl ether maleic anhydride-type copolymers with CMC or poly(ethyleneoxide), as well as denture adhesives containing CMC and poly(ethyleneoxide). See also U.S. Pat. No. 4,522,956 (issued Jun. 11, 1985) to Dhabhar and Schmidt relating to improved denture adhesives containing poly(ethyleneoxide) as the sole adhesive component in a hydrophilic vehicle comprising certain polyethylene glycols.

Other denture adhesives are described in U.S. Pat. Nos. 4,530,942 (issued Jul. 23, 1985); 4,542,168 (issued Sep. 17, 1985); and 4,569,955 (issued Feb. 11, 1986).

U.S. Pat. No. 4,529,748 to H. G. P. Wienecke (issued Jul. 16, 1985), relates to dental prosthesis adhesives formed from film-forming substances such as various cellulose derivatives, acrylate polymers, methacrylate polymers, and other film-providing substances.

U.S. Pat. No. 4,138,477 to Gaffar (issued Feb. 6, 1979) discloses oral compositions to control mouth odor containing zinc-polymer combinations formed from zinc reacted with an anionic polymer containing carboxylic, sulfonic and/or phosphonic acid radicals.

Although many different approaches have been taken to formulate denture adhesives, there is still the need to develop adhesives which hold well and are more aesthetically pleasing.

Yet, the search continues for denture adhesives that will provide the above-described characteristics and, importantly, will maintain the secure fit of the denture.

In accordance with the present invention, improved aesthetic characteristics are obtained in a denture adhesive composition by using a hydrophilic adhesive powder and a liquid vehicle that cures to a peelable solid.

It is an object of the present invention to provide improved denture adhesives which are easy to manufacture and that will be stable over prolonged periods in the oral cavity, yet will allow easy removal of the denture on demand.

It is a further object of the present invention to provide denture adhesive compositions which provide the user with greater ease of removal of the adhesive from the dentures.

It is a further object to provide such adhesives using toxicologically-acceptable, palatable materials.

It is another object herein to provide adhesives that perform well in the presence of moisture, particularly in the presence of body fluids such as saliva, perspiration and blood.

These and other objects are secured by the present invention, in the manner disclosed hereinafter.

All percentages and ratios herein are by weight and all measurements are made at 25° C. unless otherwise specified.

SUMMARY OF THE INVENTION

The present invention encompasses adhesive compositions comprising a hydrophilic adhesive powder and a liquid vehicle that cures to a peelable solid.

DETAILED DESCRIPTION OF THE INVENTION

The invention relates to denture adhesive compositions which may react within the oral cavity to form a peelable solid-like product that has superior aesthetic characteristics.

The compositions consist of two essential components.

The first is a hydrophilic adhesive powder fraction (such as salts of lower alkyl vinyl ether/maleic anhydride copolymers, sodium carboxy methylcellulose, polyethylene oxide, karaya gum, polyethylene glycol, polyamines, polyvinyl pyrolidone, guar gum, sodium alginate, polyvinyl alcohol, polysaccharides, hydroxy ethyl cellulose, chitosan, polyacrylic acid salts, carbopol and/or polyquats). The second is a liquid vehicle (such as 1- or 2-part Room Temperature Vulcanizable (RTV's), silicone RTV's, polyvinyl siloxanes, polyethers, polyethenes, polysulfides and/or epoxies) that cures to a peelable solid.

With regard to the hydrophilic adhesive fraction, the mixed partial salts of lower alkyl vinyl ether-maleic anhydride-type copolymers, sodium carboxymethylcellulose, polyethylene oxide homopolymers, polyethylene glycol homopolymers, and karaya gum are well known and have been used heretofore as adhesives to secure dentures.

In U.S. Pat. No. 5,073,604, Dec. 17, 1991, issued to K. Holeva et al. (incorporated herein by reference) there are described certain hydrophilic materials comprising mixed partial salts of lower alkyl vinyl ether-maleic anhydride-type copolymers. These partial salts can be utilized as all or part of the hydrophilic adhesive fraction.

The preparation of such a salt is described in Example I of the U.S. Pat. No. 5,073,604 wherein the methylvinylether/malic anhydride (MVE/MA) copolymer is neutralized up to 47.5% with calcium ion and 17.5% with zinc ions. Similarly Example II describes the preparation of 68% Ca/2% Zn, 50% Ca/20% Zn, 50% Ca/20% Zn/5% Na and 44% Ca/19% Zn/6% Na. Example V describes the preparation of various adhesive powders using Ca/Zn, Ca/Zn/NA salts, karaya gum, sodium CMC, sodium borate, sodium alginate, PVP and Gantrez acid. Compositions such as these can be used as the hydrophilic fraction of the present invention.

Commercially available MVE/MA copolymers suitable for use in making the salts include those supplied by GAF ("Gantrez" series) and Daicell.

Sodium carboxymethylcellulose gums are more fully described in "Chemical and Physical Properties: Cellulose Gums," 1978, published by Hercules, Incorporated, Coatings and Specialty Products Department, 910 Market Street, Wilmington, Del. 1989 (incorporated herein by reference).

Examples of commercially available sodium carboxymethylcellulose gums suitable for use in this invention are those sold by Hercules, Incorporated, Wilmington, Del., as types 4H1, 7H, 9H4, 7H3S, 7H0F and 7H4. Type 7H3S is preferred for use in this invention.

The ethylene oxide homopolymers possibly employed in the compositions of the invention are water soluble nonionic polyethylene oxide (PEO) homopolymers having molecular weights of from about 100,000 to about 5,000,000. These polymers are white powders, which, when moistened with water, become hydrated to form a gelatinous mass with adhesive characteristics.

Poly(ethylene oxide) homopolymers of this type are more fully described in "Polyox," 1978, published by Union Carbide Corporation, 270 Park Avenue, New York, N.Y. 10017, as Technical Bulletin F-44029B (incorporated herein by reference).

Examples of commercially available powdered poly(ethylene oxide) homopolymers suitable for use in this invention are those polymers sold by Union Carbide Corporation under the trademark POLYOX as grades WSR N-10, WSR N-80, WSR N-750, WSR N-3000, WSR-205, WSR -1105 and WSR -301.

With regard to the hydrophilic powder component, karaya gum is also well known and commercially available. Karaya gum is an adherent natural gum, readily available as a fine powder and used heretofore to secure dentures. It has the ability to swell many times its original volume upon the addition of water to form a gelatinous or mucilaginous mass.

In the compositions of this invention the adhesive component preferably comprises an effective adhesive amount of an admixture of (i) a mixed, partial salt of lower alkyl vinyl ether-maleic anhydride type copolymer (ii) CMC, (iii) PEO and/or (iv) karaya gum.

With regard to the liquid vehicle component (that cures to a peelable solid), one material found useful is an RTV. One or two part RTV's are commonly used in several industries. In dentistry they are used as a dental impression material. Medical grade RTV's are used to encase pacemakers for heart patients and to coat catheters. In the electrical and electronics industries RTV's are used as encapsulates to protect delicate circuitry. Applications in the automotive industry include the use of RTV sealants for windshield installations and RTV automated gasket-forming operations. In construction, RTV sealants are used in glazing, sealing, and caulking applications.

In this current invention these RTV's are used as a liquid vehicle that cures to a peelable solid in the mouth. This eliminates the ooze, grittiness and unpleasant texture and mouth feel associated with conventional denture adhesive creams and liquids. Also, this makes the product easy to clean by peeling. These liquid vehicles can be silicones, polyethers, polysulfides, or epoxies that cure from a liquid to a peelable solid by chemical cross-linking.

Alternatively these liquids can also be reversible hydrocolloids such as agar-based elastomers which become viscous liquids in boiling water and set to an elastic gel when cooled below 35° C.

In "The Encyclopedia of Chemical Technology" by Kirk-Othmer, Third edition, John Wiley & Sons, 1978 (incorporated herein by reference), are described certain silicone, polyether, polysulfide, and epoxy RTV's and agar-based reversible hydrocolloids. These compositions may be utilized as the liquid vehicle (that cures to a peelable solid) in this invention.

In "Silicon Compounds Register and Review" by Petrarch Systems, 1987 (incorporated herein by reference), are described certain silicone RTV's and polymer ingredients that make up these RTV's. Their compositions may also be utilized as the liquid vehicle in this invention.

Silicone fluids, gums, greases and resins which are not RTV's can optionally be included. Suitable silicone fluids are disclosed in U.S. Pat. No. 4,741,855, May 3, 1988 to Grote et al. This patent is incorporated herein by reference. Suitable silicone fluids are also disclosed in Japanese patent application number Hei 1-308234 to Hitoshi Matsumoto filed Nov. 28, 1989. This patent is incorporated herein by reference.

Examples of commercially available silicone RTV's may be those sold by McGhan-Nusil Corporation, California (Grades CF15-2186, CF13-2186, CF21-2186 and MED 6382). Examples of commercially available silicone polymers, catalysts and filters that can be blended to form suitable RTV's are those sold by Bayer/Miles Inc., Pennsylvania (Baysilone U polymers, Baysilone U crosslinking agents, Baysilone U catalyst Pt/6 and Baysilone basic compounds), Hulls/Petrarch America, New Jersey (catalyst PC075, polymers PS 443, PS 123 and silica SS0216), Union-Carbide (polymers Y12133, Y12134, Y12135, and Y12136), General Electric Company, Dow Corning Inc., Shiatsu Japan, Rhone-Poulenc France and Wacker Silicones Germany, Degussa U.S.A. (various grades of silica), Cabot. Corp. (silica) and Quarzwerke-Germany (cristo balite).

The compositions of the present invention can optionally include from about 0.01% to about 5% of one or more components which provide the user with sensory, including flavor, benefits. Suitable components include menthol, menthyl lactate, peppermint oil, spearmint oil, peppermint oil, leaf alcohol, as well as those paramenthane carboxyamides flavoring agents available from Wilkinson-Sword (such as WS-3) which are described in U.S. Pat. No. 4,136,163 to Watson et al., issued Jan. 23, 1979 which is incorporated by reference herein.

The compositions of the present invention are manufactured in an art-recognized manner known to those skilled in the art, such as in a powder, cream, ointment, liquid or a paste. Suitable examples of such formulations are disclosed in U.S. Pat. No. 4,518,721, issued May 21, 1985 and U.S. Pat. No. 4,514,528, issued Apr. 30, 1985, both to Dhabhar et al. and both of which are hereby incorporated by reference herein.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

This example illustrates the compounding of a denture adhesive composition that uses a 2-part liquid that cures to peelable solid upon mixing the 2 parts.

Into two 200 cc beakers are weighed 65 gm each of a silicone RTV Part 1 and Part 2 (McGhan-Nusil Ultra-fast cure silicone elastomer CFI5-2186 and/or CF13 and/or CF21). To a separate 100 cc glass jar, 42 gms of Ca (47.5)/Zn (17.5) Gantrez salt and 28 gm of sodium CMC (Grade 7H3SX8F from Hercules) are added. This jar is then shaken well to ensure intimate mixing of the 2 powders. 35 grams of this powder blend is added to Part 1 of the RTV and the other 35 grams to Part 2 of the RTV. These powder additions are then compounded into the silicone RTV (Part 1 and Part 2 separately) using a spatula. This mixing is continued for a minimum of 5 minutes until a smooth, homogenous dispersion is obtained.

The above 2-part denture adhesive liquid when mixed together and applied on the dentures, sticks to the dentures, sticks to the oral tissue and cures to form a peelable solid. This peelable solid does not ooze, locks food out and is very easy to clean (by peeling) from the dentures and mouth.

EXAMPLE II

This example illustrates the compounding of a denture adhesive composition that uses a 2-part liquid that cures to a peelable solid upon mixing the 2 parts.

Into a 200 cc beaker is weighed 60 gms of Part 1 of a silicone RTV (McGhan-Nusil silicone elastomer CF15-2186 and/or CF13-2186 and/or CF21-2186). Into a second 200 cc beaker is weighed 100 gms of Part B of the silicone RTV.

To a separate 100 cc glass jar, 24 gms of Ca (47.5)/Zn(17.5) Gantrez salt and 16 gms of sodium CMC (grade 7H3SX8F from Hercules) are added. This jar is then shaken well to ensure intimate mixing of the 2 powders. This 40 gms of powder blend is added to 60 gms of Part 1 of the silicone RTV and compounded using a spatula. This mixing is continued for a minimum of 5 minutes until a smooth, homogenous dispersion is obtained.

The above 2-part denture adhesive liquid when mixed together and applied on the dentures sticks to the dentures, sticks to the oral tissue and cures to form a peelable solid. This peelable solid does not ooze, locks food out and is very easy to clean (by peeling) from the dentures and mouth.

EXAMPLE III

This example illustrates the compounding of a denture adhesive composition that uses a 1-part RTV that is activated by moisture/saliva to form a peelable solid.

Into a 200 cc beaker is weighed 80 grams of a 1-part silicone RTV (Dow Corning silastic medical adhesive Cat. No. 891). To this 20 gms of Ca/Zn Gantrez salt of Example I is added. This powder additive is then compounded into the RTV using a spatula. This mixing is continued for a minimum of 5 minutes until a smooth homogenous dispersion is obtained.

The above 1-part denture adhesive when applied on the denture sticks to the dentures, sticks to the oral tissue and cures upon contact with saliva to form a peelable solid. This peelable solid does not ooze, locks food out and is very easy to clean (by peeling) from the denture and mouth.

EXAMPLE IV

This example illustrates the compounding of a denture adhesive liquid composition that uses a 2-part RTV and a silicone oil diluent.

The procedure of Example I is repeated except that 40 grams of each of the silicone RTV Part 1 and Part 2 are used in conjunction with 25 grams of a silicone oil (Dow Corning 245 fluid) as a diluent.

The above 2-part low viscosity denture adhesive liquid when mixed together and applied on the dentures, sticks to the dentures, sticks to the oral tissue and cures to form a peelable solid. This peelable solid does not ooze, locks food out and is very easy to clean (by peeling) from the dentures and mouth.

EXAMPLE V

This example illustrates the compounding of a denture adhesive composition that uses a condensation cured, silicone RTV.

The same procedure of Example IV is repeated except that the Ca/Zn Gantrez salt is added to the base liquid of a 2-part condensation cured silicone RTV (MED 6382 from McGhan-Nusil). When this blend is exposed to a tin catalyst it cures to a peelable solid.

The above 2-part denture adhesive liquid when mixed together and applied on the dentures, sticks to the dentures, sticks to the oral tissue and cures to form a peelable solid. This peelable solid does not ooze, locks food out and is very easy to clean (by peeling) from the dentures and mouth.

EXAMPLE VI

The compounding procedure in Example I or II is repeated with the following ingredients:

|  | A (%) | B (%) | C (%) |
|---|---|---|---|
| 2-part Addition Cured Silicone RTV | 65 | 65 | 65 |
| Ca/Zn Gantrez Salt | 0 | 35 | 0 |
| CMC | 35 | 0 | 14 |
| Ca/Na Gantrez Salt | 0 | 0 | 21 |

In use, the above 2-part liquids/creams are placed on a dry or wet denture, and the denture is inserted in the mouth and pressed into place.

EXAMPLE VII

The compounding procedure in Example V is repeated with the following ingredients:

|  | A (%) | B (%) | C (%) |
|---|---|---|---|
| 2-part Condensation Cured Silicone RTV | 65 | 65 | 65 |
| Ca/Zn Gantrez Salt | 0 | 35 | 0 |
| CMC | 35 | 0 | 14 |
| Ca/Na Gantrez Salt | 0 | 0 | 21 |

In use, the above 2-part liquids/creams are placed on a dry or wet denture, and the denture is inserted in the mouth and pressed into place.

EXAMPLE VIII

|  | A (%) | B (%) | C (%) |
|---|---|---|---|
| 2-part Addition Silicone RTV | 40 | 40 | 0 |
| Ca/Zn Gantrez Salt | 21 | 21 | 30 |
| CMC | 14 | 14 | 20 |
| Silicone Oil | 25 | 0 | 50 |
| Vinyl End Blocked Poly Dimethyl Siloxane | 0 | 25 | 0 |

In use, the above 2-part liquids/creams are placed on a dry or wet denture, and the denture is inserted in the mouth and pressed into place.

EXAMPLE IX

This example illustrates the compounding of a denture adhesive composition that uses a vinyl-terminated polydimethyl siloxane, platinum catalyst, silica and polydimethyl siloxanes containing Si-H groups to generate the RTV vehicle.

Into a 200 cc breaker is weighed 38.74 grams of a vinyl terminated polydimethyl siloxane (Baysilone UI), 26 grams of silica (silbond RST and Aerosil Rg74 or SS0216)0.26 grams of platinum-silicone complex catalyst (PC075) and 35 grams of Ca/Zn Gantrez salt. This is mixed with a spatula for a minimum of 5 minutes until a smooth, homogenous dispersion is obtained.

Into a second 200 cc beaker is weighed 34.5 grams of Baysilone UI, 26 grams of silica, 4.5 grams of Baysilone 430 and 35 grams of Ca/Zn Gantrez salt. This is mixed with a spatula for a minimum of 5 minutes until a smooth, homogenous dispersion is obtained.

The above 2-part denture adhesive liquid/cream when mixed together and applied on the dentures, sticks to the dentures, sticks to the oral tissue and cures to form a peelable solid. This peelable solid does not ooze, locks food out, and is very easy to clean (by peeling) from the dentures and mouth.

What is claimed is:

1. A denture adhesive composition which adheres to dentures and oral tissue comprising a mixture of:
   (a) from about 8% to 90% of a hydrophilic powder selected from the group consisting of mixed partial salts of alkyl vinyl ether maleic anhydride copolymers (AVE/MA), sodium carboxymethylcellulose (CMC), polyethylene glycol (PEG), sodium alginate, hydroxyethylcellulose (HEC), chitosan, acid form of alkyl vinyl ether maleic anhydride copolymer, carbopol polymers, polyvinyl alcohol, polyamines, polyquaternary compounds, and mixtures thereof; and
   (b) from about 10% to 92% of a part silicone RTV liquid that cures to form a peelable solid upon mixing the 2 parts.

2. The composition of claim 1 wherein component (a) comprises mixed partial salts of AVE/MA, CMC, PEO, karaya gum and/or HEC and component (b) is a 1- or 2-part silicone RTV that cures by 2-part mixing and/or exposure to saliva/water.

3. The composition of claim 2 wherein component (b) is an addition cured 2-part silicone RTV wherein part 1 is a blend of vinyl functional silicone polymers, and a platinum catalyst and/or silica and/or inhibitors; and part 2 is a blend of vinyl functional silicone polymers, and a hydride functional siloxanes and/or silica.

4. The composition of claim 2 wherein component (b) is an addition cured 2-part silicone RTV wherein part 1 is a blend of vinyl-terminated polydimethyl siloxane, and a platinum-divinyltetramethyldisiloxane complex catalyst and/or silica; and part 2 is a blend of vinyl-terminated polydimethylsiloxane, and a polydimethylsiloxane polymer containing Si-H groups and/or silica.

5. The composition of claim 2 wherein component (b) is a 2-part condensation cured silicone RTV wherein part 1 is a blend of silanol-terminated silicone polymers, and alkoxy functional silicon compounds, and silica and/or diatomaceous earth; and part 2 is a tin and/or zinc catalyst.

6. The composition of claim 2 wherein component (b) is a 2-part condensation cured silicone RTV wherein part 1 is a blend of silanol-terminated silicone polymers, and hydride functional siloxanes, and silica and/or diatomaceous earth; and part 2 is a tin and/or zinc catalyst.

7. The composition of claim 2 wherein component (b) is a 1-part silicone RTV that cures by exposure to saliva/water with or without a basic additive to neutralize the acidic by-products.

8. The composition of claim 2 wherein component (b) is converted to a 1-part system via microencapsulation.

9. A denture adhesive composition which adheres to dentures and oral tissue comprising a mixture of:
- (a) from about 8% to 90% of a hydrophilic powder selected from the group consisting of AVE/MA (neutralized with calcium, zinc, sodium, strontium, iron and/or magnesium), CMC, HEC and mixtures thereof; and
- (b) from about 10% to 92% of a 2-part silicone RTV liquid that cures to form a peelable solid upon mixing the two parts or a 1-part silicone RTV liquid that cures to form a peelable solid upon exposure to moisture/saliva.

10. The composition of claim 9 wherein (a) is a mixed partial salt of AVE/MA copolymer (neutralized with calcium, zinc and/or sodium) and/or CMC.

11. The composition of claim 9 wherein (b) is a 2-part silicone RTV.

12. The composition of claim 1 which further comprises from about 0.01% to about 30% of menthol, menthyl lactate, peppermint oil, spearmint oil, leaf alcohol, paramenthane carboxyamides, dyes and colorants, antibacterial additives and mixtures thereof.

13. The composition of claim 1 which in addition contains a silicone fluid, grease, gum, resin or mixtures thereof as a component of the total composition.

14. The composition of claim 1 wherein (b) is a silicone fluid, grease, gum, resin or mixtures thereof.

15. The composition of claim 1 where (b) is a 1- or 2-part silicone RTV liquid modified to contain carboxyl, hydroxyl and/or amino functional groups.

16. A denture adhesive composition which adheres to dentures and oral tissue comprising a mixture of:
- (a) from about 8% to 90% of a hydrophilic powder selected from the group consisting of mixed partial salts of alkyl vinyl ether maleic anhydride copolymers (AVE/MAX) sodium carboxymethylcellulose (CMC), polyethylene glycol sodium alginate, hydroxyethylcellulose (HEC), chitosan, acid form of alkyl vinyl ether maleic anhydride copolymer, carbopol polymers, polyvinyl alcohol, polyamines, polyquarternary compounds, and mixtures thereof; and
- (b) from about 10% to 92% of a 1-part silicone RTV liquid that cures to form a peelable solid upon exposure to saliva/water.

* * * * *